(12) United States Patent
Fromovich et al.

(10) Patent No.: US 6,758,673 B2
(45) Date of Patent: Jul. 6, 2004

(54) PERIOSTEAL DISTRACTION

(76) Inventors: Ofir Fromovich, Moshav Adanim 28, Hod Hasharon (IL); Ben-Zion Karmon, Ben Zakai 17, Elad (IL)

( * ) Notice: Subject to any disclaimer, the term of this patent is extended or adjusted under 35 U.S.C. 154(b) by 20 days.

(21) Appl. No.: 10/002,135

(22) Filed: Dec. 5, 2001

(65) Prior Publication Data

US 2003/0104339 A1 Jun. 5, 2003

(51) Int. Cl.[7] ................................................. A61F 2/12
(52) U.S. Cl. .......................................... 433/215; 623/8
(58) Field of Search ................................ 433/215, 173, 433/189; 623/17.17, 8; 606/192, 198, 105

(56) References Cited

U.S. PATENT DOCUMENTS

| | | |
|---|---|---|
| 4,430,760 A | 2/1984 | Smestad |
| 4,501,266 A | 2/1985 | McDaniel |
| 4,755,184 A | 7/1988 | Silverberg |
| 4,787,906 A * | 11/1988 | Haris ....................... 623/23.72 |
| 4,798,205 A * | 1/1989 | Bonomo et al. ............ 606/192 |
| 4,929,247 A | 5/1990 | Rayhack |
| 4,994,298 A | 2/1991 | Yasuda |
| 5,020,525 A | 6/1991 | Ewing |
| 5,059,194 A | 10/1991 | Michelson |
| 5,152,747 A | 10/1992 | Olivier |
| 5,156,605 A | 10/1992 | Pursley et al. |
| 5,180,380 A | 1/1993 | Pursley et al. |
| 5,304,117 A | 4/1994 | Wilk |
| 5,308,350 A | 5/1994 | Mikhail |
| 5,350,580 A | 9/1994 | Muchow et al. |
| 5,380,329 A | 1/1995 | Elia et al. |
| 5,429,638 A | 7/1995 | Muschler et al. |
| 5,487,897 A | 1/1996 | Polson |
| 5,505,733 A | 4/1996 | Justin |
| 5,511,565 A * | 4/1996 | Syers ......................... 128/898 |
| 5,536,269 A | 7/1996 | Spievack |
| 5,569,308 A | 10/1996 | Sottosanti |
| 5,630,843 A | 5/1997 | Rosenberg |
| 5,655,545 A | 8/1997 | Johnson et al. |
| 5,676,664 A | 10/1997 | Alland |
| 5,681,309 A | 10/1997 | Ross, Jr. et al. |
| 5,695,338 A | 12/1997 | Robert |
| 5,700,479 A | 12/1997 | Lundgren |
| 5,704,939 A | 1/1998 | Justin |
| 5,766,173 A | 6/1998 | Ross, Jr. et al. |
| 5,769,856 A | 6/1998 | Dong et al. |
| 5,772,661 A | 6/1998 | Michelson |
| 5,807,382 A | 9/1998 | Chin |
| 5,810,812 A | 9/1998 | Chin |
| 5,839,899 A * | 11/1998 | Robinson ..................... 433/215 |
| 5,873,715 A | 2/1999 | Liou |
| 5,882,353 A * | 3/1999 | VanBeek et al. ............... 623/8 |
| 5,895,387 A | 4/1999 | Guerrero |
| 5,902,304 A | 5/1999 | Walker et al. |
| 5,935,594 A | 8/1999 | Ringeisen et al. |
| 5,941,910 A | 8/1999 | Schindler et al. |
| 5,957,953 A | 9/1999 | DiPoto |
| 5,968,043 A | 10/1999 | Ross, Jr. et al. |
| 5,976,142 A | 11/1999 | Chin |
| 5,980,252 A * | 11/1999 | Samchukov et al. ......... 433/215 |
| 5,980,522 A | 11/1999 | Koros et al. |
| 5,997,520 A | 12/1999 | Akr et al. |
| 6,019,764 A | 2/2000 | Bartee |
| 6,030,218 A * | 2/2000 | Robinson ..................... 433/173 |
| 6,033,412 A | 3/2000 | Losken et al. |
| 6,037,384 A | 3/2000 | Kakizawa |
| 6,050,819 A | 4/2000 | Robinson |

(List continued on next page.)

Primary Examiner—Todd E. Manahan
(74) Attorney, Agent, or Firm—Mark M. Friedman

(57) ABSTRACT

Devices and methods for gradual displacing of the periosteal tissue covering bones. The gap developing between the bone and the displaced periosteal tissue will be filled with bone callus as it is in distraction osteogenesis. The devices and methods allow formation of bone in distraction osteogenesis without cutting a segment of the bone.

121 Claims, 4 Drawing Sheets

U.S. PATENT DOCUMENTS

| | | |
|---|---|---|
| 6,113,599 A | 9/2000 | Landsberger |
| 6,126,660 A | 10/2000 | Dietz |
| 6,217,323 B1 | 4/2001 | Liou |
| 6,224,599 B1 | 5/2001 | Baynham |
| 6,280,191 B1 | 8/2001 | Gordon |
| 6,293,947 B1 | 9/2001 | Buchbinder |
| 6,302,687 B1 | 10/2001 | King |
| 6,309,220 B1 | 10/2001 | Gittleman |
| 6,322,566 B1 | 11/2001 | Minoretti et al. |
| 6,409,764 B1 * | 6/2002 | White et al. ............. 623/16.11 |

* cited by examiner

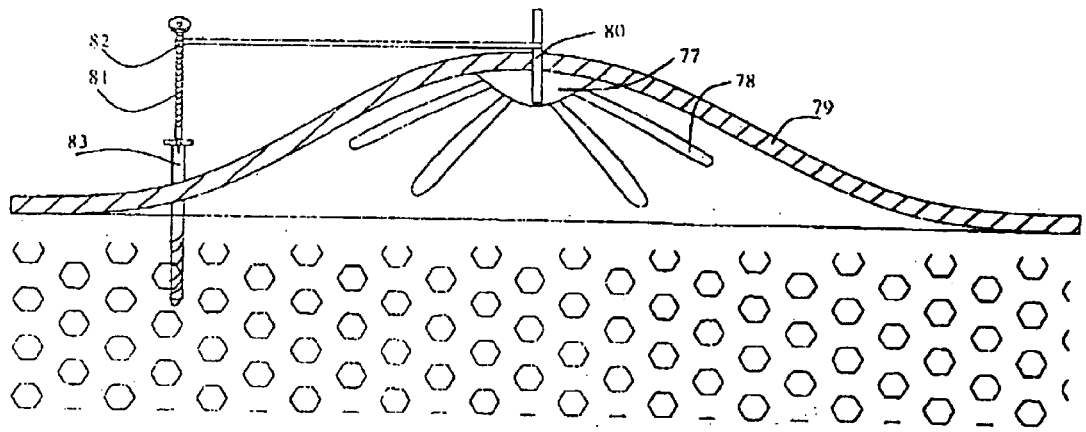
Fig. 1
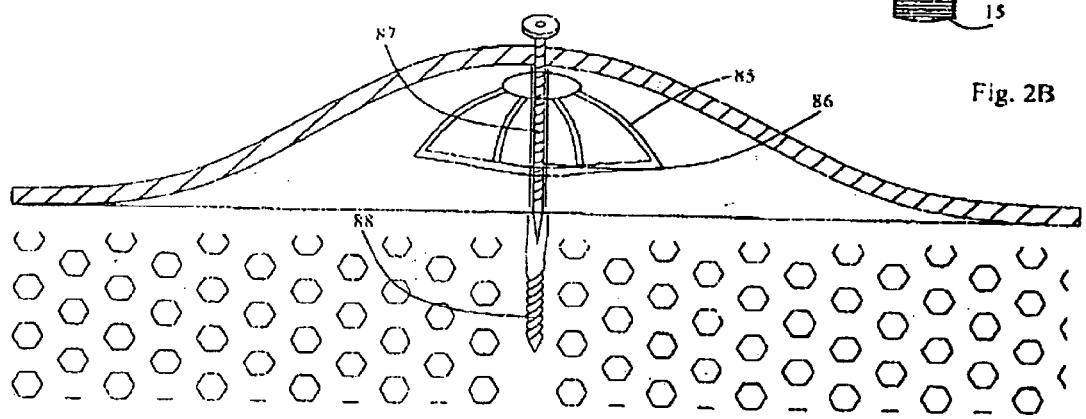
Fig. 2A
Fig. 2B
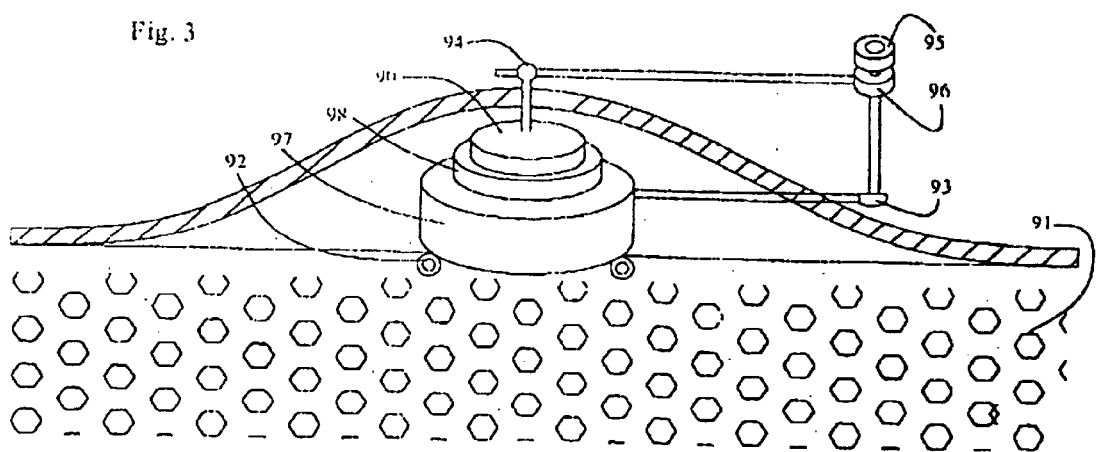
Fig. 3

PERIOSTEAL DISTRACTION

FIELD AND BACKGROUND OF THE INVENTION

The present invention relates to improved methods and devices for bone augmentation.

Treatment of edentulous patients with osseointegrated fixtures made of titanium is a well known procedure in the art. The procedure includes installing a fixture in the alveolar bone of an at least partially edentulous jaw. Usually several months are required for proper healing after fixture installation.

After healing, an abutment is installed on the upper portion of the fixture. After several weeks, an artificial tooth may be mounted on the abutment and the procedure is complete.

Installation of implants requires sufficient alveolar bone, generally about 10 mm height and 6 mm width.

When a tooth is removed, the alveolar bone is gradually resorbed because of the absence of stimulus of ossification-inducing pressure from the teeth. As the resorption process advances, the size of the bone gets reduced, i.e. the bone on which the dental roots are positioned—the alveolar ridge start shrinking.

The absence of just one tooth can cause modifications throughout the dental arch and even prompt a possible softening (loss of insertion) which may cause the loss of other teeth. The absence of several teeth aggravates the problem. Bone loss may finally modify the patient's appearance and, depending on the loss, may make him incapable of receiving bridges, implants or even dentures.

It is then necessary to carry out several surgical operations to reconstruct the alveolar ridge of the maxilla or mandible.

Although these methods of surgical reconstruction have been successfully performed, this type of operation has had drawbacks. Certain methods have involved opening the periosteal tissue (which is the tissue surrounding the bone and is easily detached from the bone) along the entire length of the atrophic alveolar ridge and then placing a bone graft material and a membrane on top of the graft and then suturing the delicate periosteal tissue back together to cover the membrane. The role of the membrane is to maintain the bone graft in its place and to prevent the mucoepithelium from growing into the graft and interfering with the process of bone regeneration. This surgical operation called guided bone regeneration has had drawbacks resulting from the lack of enough soft tissue to cover the enlarged bone.

In order to overcome some of these drawbacks, another small surgical procedure is done before the performance of the procedures mentioned above. In this procedure an expandable device is placed beneath the periosteum through a small incision. This device made of silicon is gradually filled with a liquid through a cannula. While this expandable device expands tension is transferred to the periosteum leading to enlargement of the periosteum. When the periosteum reached the desired dimension the expandable device is taken out and a bone graft is placed as described above, but now there is no need to stretch the mucoperiosteal tissue therefor reducing the complications.

This procedure has two significant drawbacks:
1. Two surgical procedures are needed. A small procedure for insertion of the expandable device and a big procedure for placing the bone graft and the membrane.
2. All the hazards of a relative big operation in the mouth.

Another method to regenerate bone is distraction osteogenesis, which is a process whereby bone is stretched to increase bone volume. According to distraction osteogenesis processes, at least one portion of a bone is at least partially separated from the bone. The position of the portion is gradually altered with respect to the bone. Time is then provided for new bone to fill in the space between the portion and the overall bone.

When distraction osteogenesis is used in dentistry dental applications, a portion of a patient's jawbone will be at least partially severed from the overall jawbone. The jawbone segment may then be gradually separated from the rest of the jawbone. New bone then fills in the space between the segment and the jawbone. By increasing the volume of bone in the jawbone, additional area can be provided to anchor or at least more securely anchor dental implants. Distraction osteogenesis can also be used in dental applications simply to strengthen a location on the jawbone to increase the bone volume at that location even if implants are not to be secured in the jawbone at that location. These techniques of distraction osteogenesis has some disadvantages:

1) It is difficult technically to the surgeon.
2) It is traumatic to the patient.
3) This procedure can be done if the height of the ridge is at least 6 mm
4) This technique is not using the new materials available today that enhance bone regeneration.

The present invention is unique because these methods and devices allow distraction osteogenesis without cutting a segment of the bone therefore the procedure is simple minimal invasive and not traumatic. In the present invention only the periosteal tissue is separated from the bone. In another embodiment of the invention materials that enhance bone regeneration can be added to the distraction gap.

SUMMARY OF THE INVENTION

The present invention provides a method and device to regenerate bone. The device is preferably made from a plate placed subperiostealy and a force inducing mechanism to allow gradual displacement of the periosteal tissue from the bone. The device can be made fully or partially of a bioresorbable material.

The device is activated one or more times every few days till the desired enlargement is reached. While the plate moves it conducts tensile forces to the surrounding tissue, which reacts in proliferation and enlargement. The gap between the plate and the bone is filled with bone callus if the periosteal tissue is displaced slowly. At the same time bone substitute materials can be added through a filling element. After the desired enlargement is reached the filling element can be pull out if necessary. The end result is a new or an enlarge compartment in the body filled with new bone callus and bone substitute materials.

The insertion of the device can be through a small incision to a subperiosteal tunnel so all the process is done with almost no surgery.

There are many possible implementations of the device and method depending on several factors:

1. The place the device is inserted into.
2. The filling material.
3. The shape of the plate.
4. The kind of filling element that is in use.
5. The kind of material the plate is made of.

The devices and methods are particularly useful for plastic surgery, orthopedic surgery and, dental implantology. Other objects and features of the present invention will become apparent in the following detailed description when taken in connection with the accompanying drawings which disclose one embodiment of the invention. It is to be understood that the drawings are designed for the purpose of illustration only and are not intended as a definition of the limits of the invention.

Thus, according to the teachings of the present invention there is provided, a method for expanding, stretching or displacing bone tissue comprising: (a) inserting subperiostealy at least part of a displacing device comprising a movable subperiosteal element and a force inducing mechanism configured after activation so as to move the movable subperiosteal element; the movable subperiosteal element is configured after activation of the force inducing mechanism so as to induce forces displacing at least part of the periosteal tissue. (b) activating said force inducing mechanism.

According to a further feature of the present invention the activation is performed in a plurality of stages separated by at least a number of hours, each stage incrementally displacing the periosteal tissue.

According to a further feature of the present invention, the displacing is done continuously over a period of time.

According to a further feature of the present invention, the speed of the displacing of the periosteal tissue is appropriate for formation of bone callus between the bone tissue and the periosteal tissue.

According to a further feature of the present invention, the force inducing mechanism induces forces continuously.

According to a further feature of the present invention, the force inducing mechanism is a pump.

According to a further feature of the present invention, the force inducing mechanism is pressure beneath the movable subperiosteal element.

According to a further feature of the present invention, the activation is done by introducing a biocompatible filling material beneath the movable subperiosteal element.

According to a further feature of the present invention, the displacing is combined with introducing a biocompatible filling material beneath the movable subperiosteal element.

According to a further feature of the present invention, the biocompatible filling material includes material for promoting the growth of bone.

According to a further feature of the present invention, the biocompatible filling material includes material for promoting the growth of bone.

According to a further feature of the present invention, the displacing device includes a filling conduit partially inserted into the tissue.

According to a further feature of the present invention, the filling conduit includes a one-directional valve.

According to a further feature of the present invention, the filling conduit includes a sealing means for sealing the filling conduit.

According to a further feature of the present invention, the method further comprising introducing disinfecting material into the filling conduit.

According to a further feature of the present invention, the filling conduit includes at least one fixation component configured to allow fixation of the filling conduit to the tissue.

According to a further feature of the present invention, the displacing device is formed at least in part from a bio-dissipative material.

According to a further feature of the present invention, the displacing device is formed at least in part from a self-expanding material.

According to a further feature of the present invention, the displacing device is configured to influence the direction of displacement of the periosteal tissue as the displacing device is activated.

According to a further feature of the present invention, the displacing device is configured to prevent displacement of the periosteal tissue not in the direction.

According to a further feature of the present invention, the displacing device is configured to take a specific shape as the force inducing mechanism is activated.

According to a further feature of the present invention, the displacing device is configured to grow in a telescopic pattern.

According to a further feature of the present invention, the displacing device is formed at least in part from a stretchable material.

According to a further feature of the present invention, at least part of the periosteal tissue is covered by a rigid structure so as to guide the periosteal tissue to take the shape of the rigid structure as the periosteal tissue is displaced.

According to a further feature of the present invention, the displacing device is formed with at least one fixation feature.

According to a further feature of the present invention, the displacing device is glued to the tissue.

According to a further feature of the present invention, the displacing device is inflatable.

According to a further feature of the present invention the displacing device becomes inflatable after insertion subperiostealy.

According to a further feature of the present invention, the activating is done by turning a screw.

According to a further feature of the present invention, the activating is done by taking an inhibiting component out.

According to a further feature of the present invention, the activating is done by allowing a bio-dissipative inhibiting component to disperse.

According to a further feature of the present invention, the force inducing mechanism comprising magnetic forces.

According to a further feature of the present invention, the movable subperiosteal element is formed at least in part from a magnetic material.

According to a further feature of the present invention, the movable subperiosteal element is enclosed in a biocompatible casing.

According to a further feature of the present invention, the activating is done outside the tissue. According to a further feature of the present invention, the activating is done inside the tissue.

According to a further feature of the present invention, the force inducing mechanism comprising forces induced by turning a screw.

According to a further feature of the present invention, the screw is hollow and perforated.

According to a further feature of the present invention, the force inducing mechanism comprising a compressed element trying to become not compressed.

According to a further feature of the present invention, the compressed element comprising a coil.

According to a further feature of the present invention, the activation is made by a biocompatible material enclosed in a bio-dissipative casing; the biocompatible material becomes active after the casing starts to disperse.

According to a further feature of the present invention, the activation is made by temperature changes.

According to a further feature of the present invention, the movable subperiosteal element is configured so as to allow passage of materials from the periosteal tissue.

According to a further feature of the present invention, the device is configured to allow passage of materials between the exterior space of the device and the interior space of the device.

According to a further feature of the present invention, the displacing device comprising a reference element and the force inducing mechanism induces forces between the reference element and the movable subperiosteal element.

According to a further feature of the present invention, the reference element is fixated to the bone.

According to a further feature of the present invention, the reference element is a bone implant.

According to a further feature of the present invention, the reference element is connected to the movable subperiosteal element by a hinge.

According to a further feature of the present invention, the hinge configured as to allow movement only in one direction.

According to a further feature of the present invention, the reference element is fixated to a tooth.

According to a further feature of the present invention, the reference element is fixated to a dental prosthesis.

According to a further feature of the present invention, the reference element is formed at least in part from magnetic material.

According to a further feature of the present invention, the reference element is gradually displaced.

According to a further feature of the present invention, the reference element includes a ball socket and the force inducing mechanism includes a screw with a ball at its edge; the ball is configured to fit inside the ball socket forming a joint so as to allow control on the position of the screw.

According to a further feature of the present invention, the force inducing mechanism includes forces induced by manual pulling.

According to a further feature of the present invention, the displacing device is a double sheet concave balloon.

According to a further feature of the present invention, the displacing device is configured so as to prevent movement of the movable subperiosteal element towards the bone.

According to a further feature of the present invention, at least part of the displacing device is configured to be pulled out easily from the tissue.

According to a further feature of the present invention, further comprising, prior to inserting the part of the displacing device, forming a subperiosteal tunnel for insertion of the part of the displacing device.

According to a further feature of the present invention, after insertion of the part of the displacing device inside the tunnel, forming a hole in the periosteal tissue above the part of the displacing device and allowing part of the displacing device to protrude above the periosteal tissue.

According to a further feature of the present invention, after insertion of the part of the displacing device inside the tunnel, forming a hole in the periosteal tissue above the part of the displacing device and connecting part of the displacing device to protrude above the periosteal tissue.

According to a further feature of the present invention, the movable subperiosteal element includes a fixation element configured to attach the movable subperiosteal element to the periosteal tissue.

According to a further feature of the present invention, the fixation element is in the shape of an arrow.

According to a further feature of the present invention, the displacing device is used to stabilize a denture.

There is also provided according to the teachings of the present invention, a device for expanding, stretching or displacing bone tissue comprising: a biocompatible movable subperiosteal element for insertion subperiostealy and a force inducing mechanism configured after activation so as to displace the movable subperiosteal element; the movable subperiosteal element is configured after activation of the force inducing mechanism so as to induce forces displacing at least part of the periosteal tissue.

According to a further feature of the present invention, the device is configured to allow the activation to be performed in a plurality of stages separated by at least a number of hours, each stage incrementally displacing the movable subperiosteal element.

According to a further feature of the present invention, the device is configured to allow continuous displacing of the movable subperiosteal element.

According to a further feature of the present invention, the speed of the displacing of the movable subperiosteal element is appropriate for formation of bone callus between the bone tissue and the periosteal tissue.

According to a further feature of the present invention, the force inducing mechanism is a pump.

According to a further feature of the present invention, the device is formed at least in part from a bio-dissipative material.

According to a further feature of the present invention, the device is formed at least in part from a self-expanding material.

According to a further feature of the present invention, the device is configured so as to influence the direction of displacement of the periosteal tissue as the displacing device is activated.

According to a further feature of the present invention, the device is configured to prevent displacement of the periosteal tissue not in the direction.

According to a further feature of the present invention, the device is configured to take a specific shape as the force inducing mechanism is activated.

According to a further feature of the present invention, the device is configured to grow in a telescopic pattern.

According to a further feature of the present invention, the device includes a filling conduit configured for insertion of material beneath the movable subperiosteal element; the filling conduit configured so as to be accessible from outside the periosteal tissue.

According to a further feature of the present invention, the filling conduit includes a one-directional valve.

According to a further feature of the present invention, the filling conduit includes a sealing means. According to a further feature of the present invention, the filling conduit is comprising a chamber for receiving disinfecting material.

According to a further feature of the present invention, the filling conduit includes at least one fixation component configured to allow fixation of the conduit to the tissue.

According to a further feature of the present invention, the device is formed with at least one fixation feature.

According to a further feature of the present invention, the device is inflatable.

According to a further feature of the present invention, the device is configured so as to becomes inflatable after insertion subperiostealy.

According to a further feature of the present invention, the movable subperiosteal element is configured so as to allow passage of materials from the periosteal tissue.

According to a further feature of the present invention, the device is configured to allow passage of materials between the exterior space of the device and the interior space of the device.

According to a further feature of the present invention, the device is formed at least in part from a stretchable material.

According to a further feature of the present invention, the device is configured so as to be glued to the tissue.

According to a further feature of the present invention, the force inducing mechanism is configured so as to induce force by turning a screw.

According to a further feature of the present invention, the screw is hollow and perforated.

According to a further feature of the present invention, the device includes an inhibiting component configured to prevent activation of the force inducing mechanism.

According to a further feature of the present invention, the inhibiting component configured so as to be taken out.

According to a further feature of the present invention, the inhibiting component is a wire.

According to a further feature of the present invention, the inhibiting component is formed at least in part from a bio-dissipative material.

According to a further feature of the present invention, the movable subperiosteal element is formed at least in part from a magnetic material.

According to a further feature of the present invention, the movable subperiosteal element is enclosed in a biocompatible casing.

According to a further feature of the present invention, the force inducing mechanism comprising magnetic forces.

According to a further feature of the present invention, the force inducing mechanism comprising a compressed element trying to become not compressed.

According to a farther feature of the present invention, the compressed element includes a coil.

According to a further feature of the present invention, the force inducing mechanism includes a material that change its shape by temperature changes.

According to a farther feature of the present invention, the device includes a reference element and the force inducing mechanism configured so as to induces forces between the reference element and the movable subperiosteal element.

According to a further feature of the present invention, the reference element is configured so as to be fixated to the bone.

According to a further feature of the present invention, the reference element is a bone implant.

According to a further feature of the present invention, the reference element is connected to the movable subperiosteal element by a hinge.

According to a further feature of the present invention, the hinge configured as to allow movement only in one direction.

According to a further feature of the present invention, the reference element is configured so as to be fixed to a tooth.

According to a further feature of the present invention, the reference element is configured so as to be fixed to a dental prosthesis.

According to a further feature of the present invention, the reference element is formed at least in part from a magnetic material.

According to a further feature of the present invention, the reference element is configured so as to be gradually displaced.

According to a further feature of the present invention, the reference element includes a ball socket and the force inducing mechanism includes a screw with a ball at its edge; the ball is configured to fit inside the ball socket forming a joint so as to allow control on the position of the screw.

According to a further feature of the present invention, the device is a double sheet concave balloon.

According to a further feature of the present invention, the device is configured so as to prevent movement of the movable subperiosteal element towards the bone.

According to a further feature of the present invention, at least part of the displacing device is configured so as to be pulled out easily from the tissue.

According to a further feature of the present invention, the device includes a protruding element configured so as to be connected to the device after insertion subperiostealy and protrude outside the tissue.

According to a further feature of the present invention, the protruding element is configured to allow connection to other elements.

According to a further feature of the present invention, the protruding element is configured to allow introducing of materials beneath the movable subperiosteal element.

According to a further feature of the present invention, the movable subperiosteal element includes fixation element configured so as to attach the movable subperiosteal element to the periosteal tissue.

According to a further feature of the present invention, the fixation element is in the shape of an arrow.

According to a further feature of the present invention, the device includes an active biocompatible material enclosed in a bio-dissipative casing.

BRIEF DESCRIPTION OF THE DRAWINGS

The invention is herein described, by way of example only, with reference to the accompanying drawings, wherein:

FIG. 1 is a perspective view illustrating the novel device for displacing the gums with an external screw.

FIG. 2A is a perspective view illustrating the novel device for displacing the gums with an internal screw.

FIG. 2B is a sectional view illustrating a bone implant with a ball socket to control the position of the screw that is moving the displacing element.

FIG. 3 is a perspective view illustrating the novel device for displacing the gums with a telescopic form.

DESCRIPTION OF THE PREFERRED EMBODIMENTS

Figure 4A:
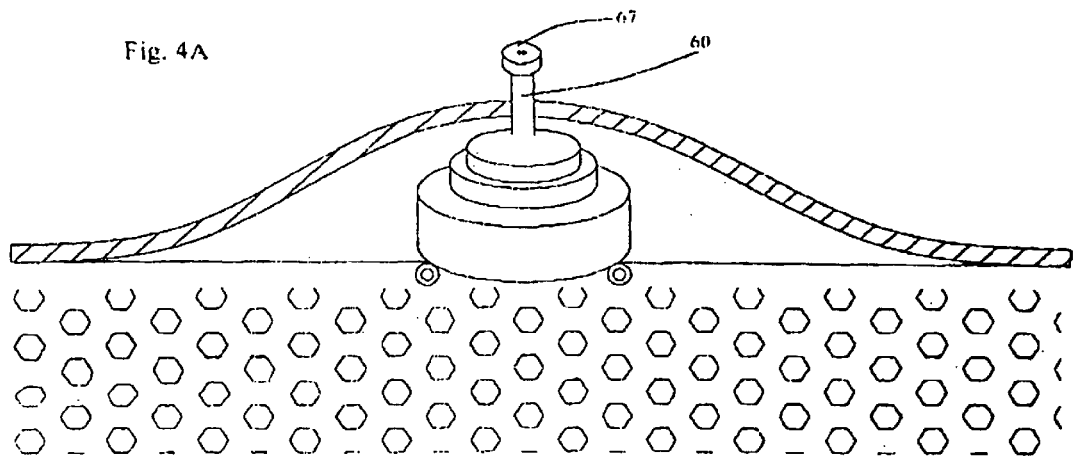
FIG. 4A is a perspective view illustrating the novel device for displacing the gums using an inflatable telescope.

As mentioned further above there are many implementations of the invention in different areas of the body. The following description will focus on embodiments for regenerating bone in the mandible in order to understand the principles of the device and method. The same principles should be used in other areas of the body.

Before turning to the features of the present invention in more detail, it will be useful to clarify certain terminology as will be used herein in the description and claims, It is noted that a large number of different types of materials are known which may be inserted within the body during a surgical procedure and which later dissipate, thereby avoiding the need for a separate surgical procedure for their removal. Such materials are properly referred to, depending upon the mechanism by which the material dissipates, as "bioresorbable", "bioabsorbable" or "biodegradable". Despite the differences between these different classes of materials, the aforementioned terminology is widely used interchangeably by medical professionals. Accordingly, and for conciseness of presentation, only one of these terms will generally be used in the following description, without implying the exclusion of the other classes of materials. Additionally, the phrase "bio-dissipative material" is used herein in the description and claims to refer generically to any and all materials which dissipate without requiring surgical removal, independent of which mechanisms such as dissolution, degradation, absorption and excretion take place. The actual choice of which type of materials to use may readily be made by one ordinarily skilled in the art, and is not generally essential to the present invention.

The term "magnetic material" is used herein to refer to a magnet or materials that are attracted by a magnet.

In the following descriptions the invention will be demonstrated on the mandible therefore the bone is down and the periosteal tissue and the gums are up. Beneath the periosteal tissue means between the bone and the displaced periosteal tissue.

Finally with respect to terminology, reference will be made to a biocompatible filling material used to fill the inflatable elements of the present invention. It should be noted that this filling material may assume a wide range of compositions and consistencies, so long as the biocompatible material may be forced into the inflatable element. Thus, possible consistencies for the filling material include, but are not limited to, consistencies described as watery, viscous, gelatinous, moldable, waxen, particulate, and suspensions or mixtures combining any of the above.

Turning now in detail to the drawings, which depict the presently preferred embodiments of the invention for the purpose of illustrating the practice thereof and not by way of limitation of the scope of the invention, and in which like reference characters refer to corresponding elements throughout the several views. FIG. 1. illustrates a basic device embodying the present invention for use in bone reconstruction and, in particular, for augmentation of atrophic alveolar ridges. The device based on external screw is composed of displacing element in the shape of a plate 77 with projections 78 located beneath the gums 79 subperiostealy and a small bar 80 that is protruding outside the tissue. This bar is connected to a screw 81 by a nut 82. The screw is placed on a stable bone implant 83. When the screw is turned the plate is moving upwards and displacing the gums. The space beneath the gums will be filled with materials from the surrounding tissue and will become bone. It is important to do the displacing slowly to allow the regeneration of the gums and also to allow the formation of a bone callus. The shape of the plate 77 and the projections are designed to allow passage of materials and blood supply from the periosteal tissue to the space developing beneath the plate 77 and projections 78 which is important for regeneration of bone. It is also important to block the passage of materials and bacteria from the oral cavity to the same space. Therefore the plate is not perforated. Any configuration of the displacing element that will have a sealed area close to the part projecting outside the gums and a perforated area distant from this projecting area will function the same.

The device can be placed by raising the periosteal tissue, placing the device on the bone and suturing the periosteal tissue on top of the device. The gums are perforated to allow the projecting part 80 is protrude to the oral cavity. In this technique activation can start several days after the insertion to allow the place of the sutures to heal. An improved technique is to create a sub periosteal tunnel insertion of the displacing device into the tunnel and perforating the gums above the displacing device to allow the projecting part to protrude to the oral cavity. In this technique activation can be done immediately after insertion since there are no sutures in the periosteal tissue to be displaced. The are some sutures only at the opening of the tunnel which is distant.

In another embodiment based on internal screw illustrated in FIG. 2B the displacing element 85 is in the shape of a dome with a tube 86 in the center protruding outside the tissue. The tube has threads compatible with a screw 87 coming from outside the tissue and standing on a bone implant 88. When the screw is turned the dome with the tube is moving upwards and displacing the gums. The advantage of this technique is that the is protruding to the oral cavity is only a screw instead of all the activation mechanism of FIG. 1 that includes the bone implant, the screw, the protruding element and the connection between them as illustrated in FIG. 1. As the protruding element is bigger it is more uncomfortable to the patient.

In another preferred embodiment illustrated in FIG. 2B The bone implant 15 can include a ball socket 16 and the screw 17 include a ball 18 at its edge to form a joint therefore allows the control on the position of the screw and the direction of the displacement.

In another preferred embodiment the device can be configured to expand in a pre designed direction and take a specific shape as it grows. For example the device can be designed in a telescopic configuration as illustrated in FIG. 3. A hollow cylinder 97 is fixated to the bone 91 by fixating screws 92. It can be also fixated by nails pushed inside the bone or glued to the bone by bone cements like calcium sulphate. Inside the hollow cylinder 97 there is a container 90 with a smaller diameter which is open towards the bone. Between the hollow cylinder and the container one or several hollow cylinders 98 can be. There are two projections from the telescope. One 93 protrudes from the lower hollow cylinder to the side and terminates in a base for a screw. This one can be outside the tissue as in FIG. 3 or can be inside the tissue. The second projection 94 is a bar that is protruding from the container upwards. This bar is connected to a screw 95 by a nut 96. The screw 95 is placed on the base for a screw 93. When the screw is turned the upper cup of the telescope is moving upwards and displacing the gums. The walls of the telescope are perforated to allow materials from the tissue to go inside the telescope. The base of the telescope is the bone so after fixating the telescope to the bone the telescope becomes inflatable. It is also possible to attach a filling conduit to the telescope to allow the insertion of materials that enhance the growth of bone tissue. The filling conduit is preferably filled with bone augmenting material in gelatinous consistency or suspension. The filling material can be an autograft, an allograft, a xenograft, an alloplast, a cytokine, a hormone, a growth factor, a physiologically acceptable drug, a biological modifier, a protein, an antigen, a cell chemotaxis stimulator material, a material inducing osteogenesis, an osteoinduction material, an osteoconduction material, a bioactive material, a bioresorbable material, a bioabsorbable material, a biodegradable material and any combination thereof. The filling material can be augmenting bone material available in the market like hydroxyapatite, bovine mineral (i.e. Bio-Oss available from Geistlich, Swiss), demineralized freezed dried bone, synthetic materials like PLA (i.e. Fisiograft from Ghimas, Spain). The filling material can be also fully or partially not bioresorbable if the procedure is done only for aesthetic reason and implants are not going to be inserted, for example crystal hydroxyapetit.

The filling material can include therapeutic materials and can include self expanding materials from the list mentioned above. Many of the bone augmenting materials have the tendency to expand when getting wet by hydration.

Another preferred embodiment, of an inflatable device that resembles the device of FIG. 3 is illustrated in FIG. 4A. The protruding part is a filling conduit 60 preferably connected to the telescope by screwing. The displacing is done by introducing a biocompatible material inside the device. The filling conduit is made of a biocompatible material and can be made from more then one type of material bioresorbable or non-bioresorbable. Preferably the filling conduit is a cannula made of commercially pure titanium or titanium alloy used in the dental implant industry. The cannula is connected to the device in one side and in the other side it can be filled and closed with a screw 67 as a sealing component. Sealing components can be also a valve, a clamping element, a knot and combination thereof. The conduit can have variable shapes, dimensions, cross section and elasticity. The filling is preferably by using a syringe that is screwed to the cannula. The cannula can have preferably fixating components in order to prevent the cannula from moving, get out and cause uncomfortable filling to the patient. The a fixation component can be selected from the group consisting of hook, hole for sutures, slot, thread, bulge, screw, change in dimension, irregularity and any combination thereof.

Figure 4B:
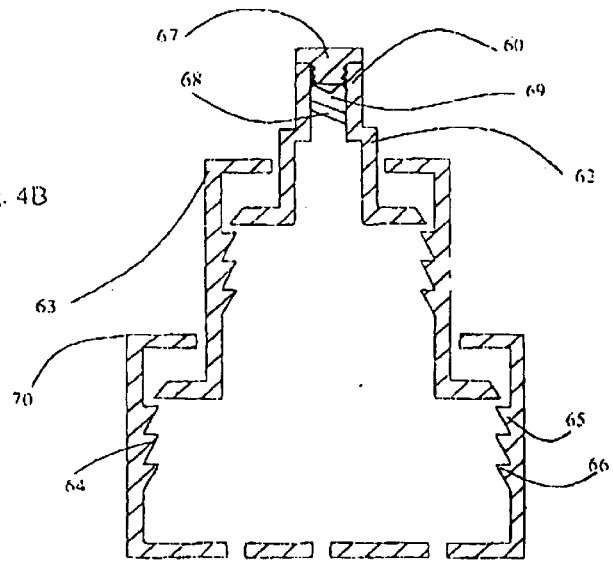
FIG. 4B is a sectional view illustrating the novel device for displacing the gums using an inflatable telescope.

The telescopic design allows to control the shape and the direction of the displaced periosteal tissue. The filling material prevent the collapse of the telescope. The telescope can have a base made from a bioresorbable material. It can be made from autograft, allograft, xenograft and alloplast and combination thereof. Preferably, the resorbable part is made of conventionally available polyglycolic acid (PGA) mesh, a high-molecular-weight linear polymer made by the ring opening polymerization of the purified glycolide monomer, although other suitable materials might be used e.g. polyglactin 910, i.e. polyglycolide co-galactide. In addition, collagen or PDS (another absorbable suture material) or cellulose might possibly also be used. The base can be also made from stiff bioresorbable materials like polylactic acid (PLA). The base is preferably has little holes to allow the penetration of bone cells. The rest of the device is preferably made from titanium. FIG. 4B is a cross section of the device of FIG. 4A. The parts of telescope are configures so the diameter of the upper region of a lower part is narrower than the diameter of the lower region of the higher part. Therefore when pulling the small container 62 upwards towards the gums till it's lower region will reach the upper region of the adjacent hollow cylinder 63 it will pull the adjacent hollow cylinder 63 upwards. Each hollow cylinder in this way will pull the next one resulting in a higher and bigger compartment with a pre designed shape. The walls can have small projections 64 on their inner side that allow only upward movement. The projections can have an incline on their lower part 65 and horizontal plain in their upper part 66. This configuration prevents changes in the shape of the device as a result of forces coming from the gums. The filling conduit 60 preferably can include a screw 67 for sealing, a one directional valve 68 and chamber 69 between them for containing disinfecting material to prevent penetration of bacteria inside the telescope. This disinfecting material preferably a biocompatible antiseptic material like chlorhexedine gel or calcium-hydroxide. The antiseptic material should be washed out before filling and put again when the cannula is closed. While introducing the biocompatible materials preferably materials that enhance bone regeneration the telescope can be pulled up manually to reduce the pressure needed for insertion of the material. In another preferred embodiment a screw is connecting the upper part 62 and the lower part 70 like the screw in FIG. 3 that can also help to reduce the pressure needed for insertion of the material. The device can include also self expanding components or materials that expands in humidity or in body temperature. Materials include, either alone or in combination, metals or metal alloys, polymers, carbon and ceramics. Exemplary metallic members include stainless steel, titanium, tantalum, shape-memory materials such as nickel-titanium alloy (NiTi) (Compounds using NiTi are manufactured under the marks NITINOL™ and ELASTINITE™ and are available from several sources), Elgiloy (trade name) and NP35N (trade designation), which can provide desired degree of springiness, malleability and/or response to temperature changes. Exemplary polymers include polyurethanes, silicon rubbers, polyether sulfones, fluoroelastomers, polyimides, polycarbonates, polyethylens, polylactic acid, polyglycolic acid, polyacrylates, and the like and combinations and copolymers thereof which provide a variety of abilities to bioabsorb or biodegrade or to be totally inert. The device can include springs and coils that are compressed before insertion and can include stretchable and elastic materials for example polyurethanes like polycarbonate urethane.

After finishing the filling process the cannula is preferably taken out and a low screw is place instead and the gums are sutures above the device. This is done to prevent infection through the cannula.

Figure 4C:
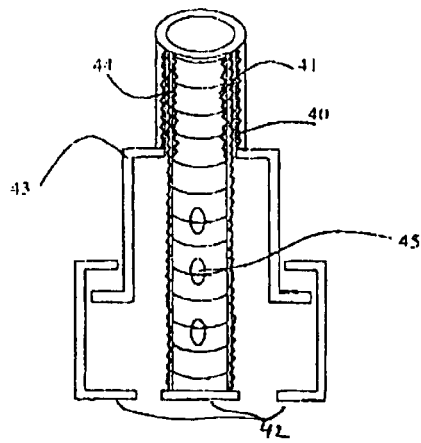
FIG. 4C is a sectional view illustrating the novel device for displacing the gums using an inflatable telescope and a hollow perforated screw for enlarging the telescope and for insertion of materials inside the telescope through the screw.

In another embodiment illustrated in FIG. 4C the cannula 40 has internal threads and a perforated hollow screw 41 can be screwed to the cannula. The screw 41 is touching the base 42 of the telescope and when activated the upper part of the telescope 43 is moving upwards. This hollow screw 41 has preferably threads 44 on its inner aspect to allow connection with a syringe. So by turning the hollow screw the telescope is growing and bone regenerating material can be easily introduced inside the telescope. This hollow screw 41 can be left inside to prevent the upper part 43 from moving toward the bone. This hollow screw can be sealed with a screw on its inner threads. The hollow screw has holes 45 in its walls to allow the bone regenerating material to get out of the hollow screw and get inside the telescope.

Figure 5:
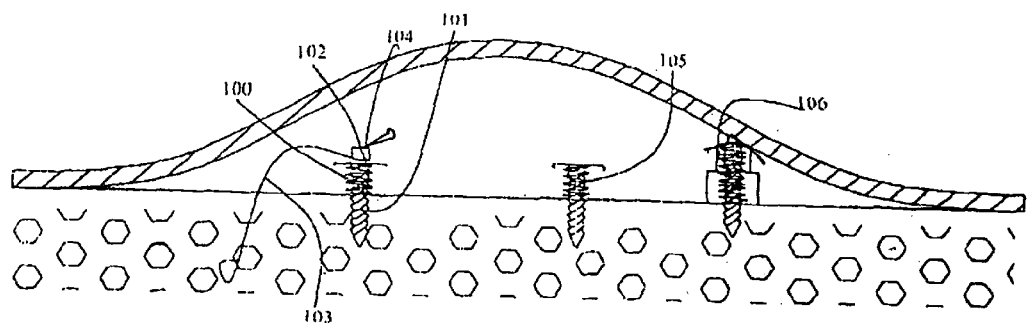
FIG. 5 is a sectional view illustrating the novel device for displacing the gums using coils.

In another embodiment based on a coil and a wire as inhibiting component illustrated in FIG. 5 a compressed coil 100 attached to a bone implant 101 is placed beneath the gums. The coil is compressed by a small plate 102 placed on the bone implant. The plate is not moving because a wire 103 is placed above the plate through a hole 104 in the bone implant and protruding outside the tissue. After the tissue is healed from inserting the implants the wire is pulled out resulting in releasing of the coil 105 and displacement of the tissue. The coil can be inside a telescope 106.

Figure 6:
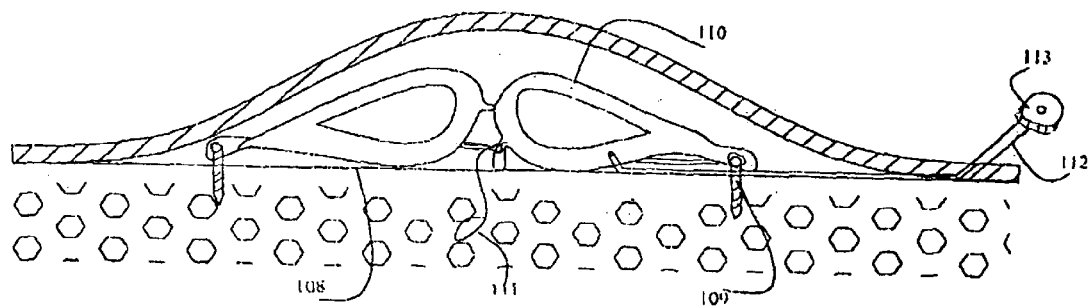
FIG. 6 is a perspective view illustrating the novel device for displacing the gums using bended rings.

In another embodiment illustrated in FIG. 6 the displacing element is composed of a large elongated ring 108 placed on the bone and fixated to the bone by screws 109. From the corners of the ring two elongated small elastic rings 110 are emerging. The angle between the large ring and the small ring is close to 90 degree when the device is passive. Before insertion of the device inside the tissue the free corners of the rings are pulled toward the large ring by a wire 111 protruding outside the tissue. When the wire is pulled out the rings try to move upwards and displace the tissue. The wire can be made from bioresorbable material therefore no need for pulling out the wire. A conduit 112 is preferably attached to the large ring and protruding outside the tissue to allow insertion of materials that promotes the growth of the bone tissue. The conduit preferably has a sealing component 113. Another preferred embodiment can use a device that the filling element for example the cannula is made of two parts one is external made of nonresorbable material and the second is internal made of bioresorbable material. The border between the two is preferably the slot. In this device it is easy to take the nonresorbable part out by twisting the cannula and leaving the bioresorbable inside the body.

Figure 7:
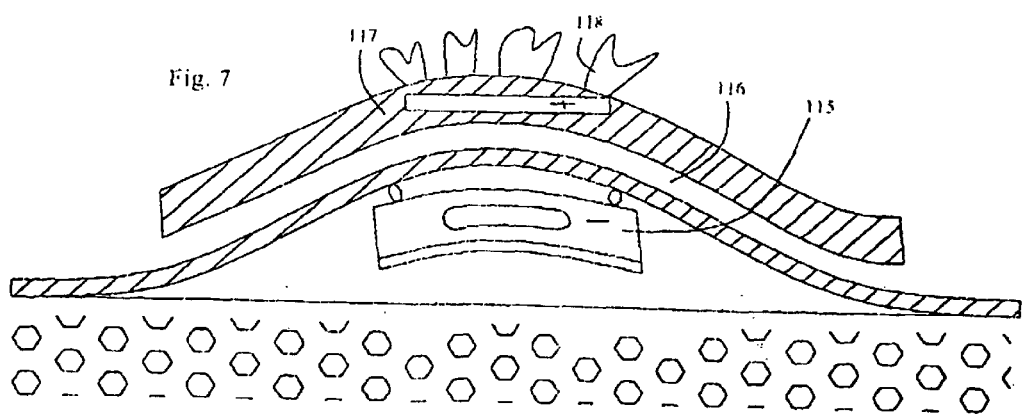
FIG. 7 is a perspective view illustrating the novel device for displacing the gums using a magnetable metal beneath the gums and a magnet inside a denture.

In another embodiment illustrated in FIG. 7 the displacing element is a magnet or a metal attracted to a magnet enclosed by a biocompatible material 115. The magnet is placed beneath the gums preferably using the tunnel technique. This metal 115 preferably fixated to the gums by sutures 116 or by projecting small arrow 120 that penetrate the tissue. This displacing element is preferably perforated to allow passage of materials from the periosteal tissue. Over the gums a denture 117 is fabricated to have a space above the gums. Inside the denture a magnet 118 is inserted so to attract the magnetable metal beneath the gums. The patient is instructed to wear the denture resulting in displacement of the gums. This method can also help to stabilize a denture without the displacement of the tissue. The magnet should be placed 1 mm above the gums and gradually pulled upwards as the gums are getting close to the magnet. Preferably the magnet is connected to a screw or a wire to allow easy displacing of the magnet. This method allows the periosteal distraction to be operated without anything projecting from the gums therefore the chances for infection. This method also allows the process to be done without manipulation inside the patient mouth. The shape of the space in the denture above the magnatable metal will dictate the shape of the periosteal tissue after displacement.

Figure 8:
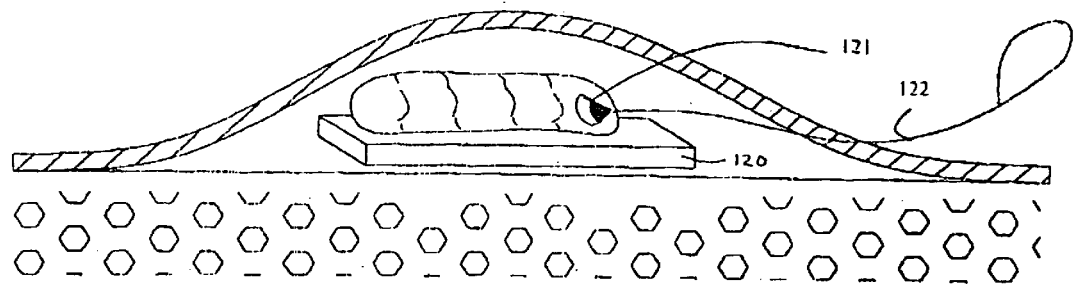
FIG. 8 is a perspective view illustrating the novel device for displacing the gums using a self expanding material.

In another embodiment illustrated in FIG. 8 the displacing element is composed of a plate 120 preferably made from stiff bioresorbable material. On top of the plate there is a material like poly (dioxanone-co-glycolide) and on top of it a catalyst enclosed in a casing 121. The casing is attached to a wire 122 allowing the puling of the casing and releasing of the catalyst. In another preferred embodiment, the casing can be made from a bioresorbable material. When the catalyst is in contact with the material in the plate a polymerization reaction starts with expansion and release of CO2. This expansion will displace the tissue. This material is also used as a bone substitute material.

Figure 9:
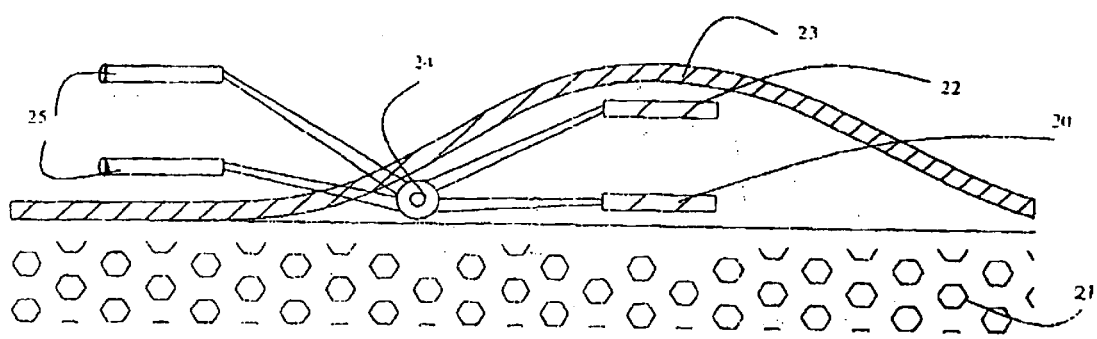
FIG. 9 is a perspective view illustrating the novel device for displacing the gums using a hinge.

In another preferred embodiment illustrated in FIG. 9 the device is made from two parts placed subperiostealy. One is a reference part 20 touching the bone 21 and the second one is a displacing element 22 touching the periosteal tissue 23. The displacing element is preferably perforated. The two parts are connected with a hinge 24. The hinge preferably allows movement only in one direction to prevent collapse of the periosteal tissue. Both parts have projections 25 outside the tissue that are configured to be attached to an external instrument. The external instrument when activated works like scissors and causing the subperiosteal element to move upwards. This displacing device can easily be pulled out from the tissue at the end of the procedure.

Figure 10:
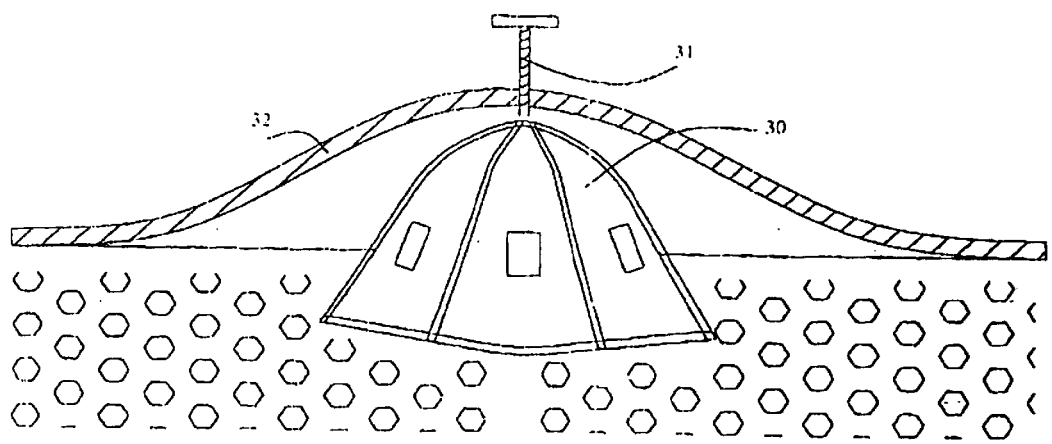
FIG. 10 is a perspective view illustrating the novel device for displacing the gums using an inflatable double sheet balloon in the shape of a dome.

In another preferred embodiment illustrated in FIG. 10 the displacing device is a concave double sheet balloon 30 connected to a cannula 31. The balloon 30 is placed subperiostealy and the cannula 31 is projecting outside the periosteal tissue 32. When the balloon is inflated it takes the shape of a dome that is perforated and the periosteal tissue 32 is elevated. The balloon can be connected to a pump therefore no need for several treatments in some hours intervals instead the inflation is continuous.

The foregoing procedure has been described in terms of the mandible. Of course, the same procedure can also be applied to reconstruction of the maxilla and other bones and for other tissues in the body.

Although the present invention has been described and illustrated in the context of certain preferred embodiments, it will be understood that modifications may be made without departing from the spirit of the invention.

What is claimed is:

1. A method for expanding, stretching or displacing bone tissue comprising:

(i) inserting subperiostealy at least part of a displacing device comprising a movable subperiosteal element and a force inducing mechanism configured after activation so as to move said movable subperiosteal element; said movable subperiosteal element is configured after activation of said force inducing mechanism so as to induce forces displacing at least part of said periosteal tissue and to create a space between said moveable subperiosteal element and the bone: said device is configured to allow ingrowth of bone tissue inside said space;

(ii) activating said force inducing mechanism.

2. The method of claim 1, wherein said activation is performed in a plurality of stages separated by at least a number of hours, each stage incrementally displacing said periosteal tissue.

3. The method of claim 1, wherein said displacing is done continuously over a period of time.

4. The method of claim 1, wherein the speed of said displacing of said periosteal tissue is appropriate for formation of bone callus between said bone tissue and said periosteal tissue.

5. The method of claim 1, wherein said force inducing mechanism induces forces continuously.

6. The method of claim 1, wherein said force inducing mechanism is a pump.

7. The method of claim 1, wherein said force inducing mechanism is pressure beneath said movable subperiosteal element.

8. The method of claim 1, wherein said activation is done by introducing a biocompatible filling material beneath said movable subperiosteal element.

9. The method of claim 8, wherein said biocompatible filling material includes material for promoting the growth of bone.

10. The method of claim 1, wherein said displacing is combined with introducing a biocompatible filling material beneath said movable subperiosteal element.

11. The method of claim 9, wherein said biocompatible filling material includes material for promoting the growth of bone and said material for promoting the growth of bone is touching the hone.

12. The method of claim 1, wherein said displacing device includes a filling conduit partially inserted into the tissue.

13. The method of claim 12, wherein said tilling conduit includes a one-directional valve.

14. The method of claim 12, wherein said filling conduit includes a sealing means for sealing said filling conduit.

15. The method of claim 14, further comprising introducing disinfecting material into said filling conduit.

16. The method of claim 14, wherein said filling conduit includes at least one fixation component configured to allow fixation of said filling conduit to the tissue.

17. The method of claim 1, wherein said displacing device is formed at least in part from a bio-dissipative material.

18. The method of claim 1, wherein said displacing device is formed at least in part from a self-expanding material.

19. The method of claim 1, wherein said displacing device is configured to influence the direction of displacement of said periosteal tissue as said displacing device is activated.

20. The method of claim 19, wherein said displacing device is configured to prevent displacement of said periosteal tissue not in said direction.

21. The method of claim 1, wherein said displacing device is configured to take a specific shape as said force inducing mechanism is activated.

22. The method of claim 1, wherein said displacing device is configured to grow in a telescopic pattern.

23. The method of claim 1, wherein said displacing device is formed at least in part from a stretchable material.

24. The method of claim 1, wherein at least part of said periosteal tissue is covered by a rigid structure so as to guide said periosteal tissue to take the shape of said rigid structure as said periosteal tissue is displaced.

25. The method of claim 1, wherein said displacing device is formed with at least one fixation feature.

26. The method of claim 1, wherein said displacing device is glued to the tissue.

27. The method of claim 1, wherein said displacing device is inflatable.

28. The method of claim 1, wherein said displacing device becomes inflatable after insertion subperiosteally.

29. The method of claim 1, wherein said activating is done by turning a screw.

30. The method of claim 1, wherein said activating is done by taking an inhibiting component out.

31. The method of claim 1, wherein said activating is done by allowing a bio-dissipative inhibiting component to disperse.

32. The method of claim 1, wherein said force inducing mechanism comprising magnetic forces.

33. The method of claim 1, wherein said movable subperiosteal element is formed at least in part from a magnetic material.

34. The method of claim 33, wherein said displacing device is used to stabilize a denture.

35. The method of claim 1, wherein said activating is done outside the tissue.

36. The method of claim 1, wherein said activating is done inside the tissue.

37. The method of claim 1, wherein said force inducing mechanism comprising forces induced by turning a screw.

38. The method of claim 37, wherein said screw is hollow and perforated said activation of said force inducing mechanism is done by turning said hollow and perforated screw.

39. The method of claim 1, wherein said force inducing mechanism comprising a compressed element trying to become not compressed.

40. The method of claim 39, wherein said compressed element comprising a coil.

41. The method of claim 1, wherein said activation is made by a biocompatible material enclosed in a bio-dissipative casing; said biocompatible material becomes active after said casing starts to disperse.

42. The method of claim 1, wherein said activation is made by temperature changes.

43. The method of claim 1, wherein said movable subperiosteal element is configured so as to allow passage of materials from said periosteal tissue.

44. The method of claim 1, wherein said device is configured to allow passage of materials between the exterior space of said device and the interior space of said device.

45. The method of claim 1, wherein said displacing device comprising a reference element and said force inducing mechanism induces forces between said reference element and said movable subperiosteal element.

46. The method of claim 45, wherein said reference element is fixated to the bone.

47. The method of claim 46, wherein said reference element is a bone implant.

48. The method of claim 46, wherein said reference element is fixated to a tooth.

49. The method of claim 46, wherein said reference element is fixated to a dental prosthesis.

50. The method of claim 46, wherein said reference element is formed at least in part from magnetic material.

51. The method of claim 50, wherein said reference element is gradually displaced.

52. The method of claim 45, wherein said reference element includes a ball socket and said force inducing mechanism includes a screw with a ball at its edge; said ball is configured to fit inside said ball socket forming a joint so as to allow control on the position of said screw.

53. The method of claim 45, wherein said reference element is connected to said movable subperiosteal element by a hinge.

54. The method of claim 45, wherein said hinge configured as to allow movement only in one direction.

55. The method of claim 1, wherein said force inducing mechanism includes forces induced by manual pulling.

56. The method of claim 1, wherein said displacing device is a double sheet concave balloon.

57. The method of claim 1, wherein said displacing device is configured so as to prevent movement of said movable subperiosteal element towards said bone.

58. The method of claim 1, wherein at least part of said displacing device is configured to be pulled out easily from said tissue.

59. The method of claim 1, further comprising, prior to inserting said part of said displacing device, forming a subperiosteal tunnel for insertion of said part of said displacing device.

60. The method of claim 59, wherein after insertion of said part of said displacing device inside said tunnel, forming a hole in said periosteal tissue above said part of said displacing device and allowing part of said displacing device to protrude above said periosteal tissue.

61. The method of claim 59, wherein after insertion of said part of said displacing device inside said tunnel, forming a hole in said periosteal tissue above said part of said displacing device and connecting part of said displacing device to protrude above said periosteal tissue.

62. The method of claim 61, wherein said fixation element is in the shape of an arrow.

63. The method of claim 1, wherein said movable subperiosteal element includes a fixation element configured to attach said movable subperiosteal element to said periosteal tissue.

64. The method of claim 1 wherein said movable subperiosteal element includes a protruding element configured to protrude through said periosteal tissue.

65. The method of claim 33, wherein said movable subperiosteal element is enclosed in a biocompatible casing.

66. A device for expanding, stretching or displacing bone tissue comprising:
a biocompatible movable subperiosteal element for insertion subperiostealy and a force inducing mechanism configured after activation so as to displace said movable subperiosteal element; said movable subperiosteal element is configured after activation of said force inducing mechanism so as to induce forces displacing at least part of the periosteal tissue and to create a space between said movable subperiosteal element and the bone;
said device is configured ingrowth of bone tissue inside said space:
said movable subperiosteal element includes a protruding element configured to protrude through said periosteal tissue.

67. The device of claim 66, wherein said device is configured to allow said activation to be performed in a plurality of stages separated by at least a number of hours, each stage incrementally displacing said movable subperiosteal element.

68. The device of claim 66, wherein said device is configured to allow continuous displacing of said movable subperiosteal element.

69. The device of claim 68, wherein the speed of said displacing of said movable subperiosteal element is appropriate for formation of bone callus between said bone tissue and said periosteal tissue.

70. The device of claim 66, wherein said force inducing mechanism is a pump.

71. The device of claim 66, wherein said device is formed at least in part from a bio-dissipative material.

72. The device of claim 66, wherein said device is formed at least in part from a self-expanding material.

73. The device of claim 66, wherein said device is configured so as to influence the direction of displacement of said periosteal tissue as said displacing device is activated.

74. The device of claim 73, wherein said device is configured to prevent displacement of said periosteal tissue not in said direction.

75. The device of claim 66, wherein said device is configured to take a specific shape as said force inducing mechanism is activated.

76. The device of claim 66, wherein said device is configured to grow in a telescopic pattern.

77. The device of claim 77, wherein said device includes a filling conduit configured for insertion of material beneath said movable subperiosteal element; said filling conduit configured so as to be accessible from outside said periosteal tissue.

78. The device of claim 77, wherein said filling conduit is the protruding element.

79. The device of claim 77, wherein said filling conduit is configured to allow said material to touch the bone.

80. The device of claim 77, wherein said filling conduit includes a one-directional valve.

81. The device of claim 77, wherein said filling conduit includes a sealing means.

82. The device of claim 81, wherein said filling conduit comprising a chamber for receiving disinfecting material.

83. The device of claim 77, wherein said filling conduit includes at least one fixation component configured to allow fixation of said conduit to the tissue.

84. The device of claim 66, wherein said device is formed with at least one fixation feature.

85. The device of claim 66, wherein said device is inflatable.

86. The device of claim 66, wherein said device is configured so as to becomes inflatable after insertion subperiostealy.

87. The device of claim 66, wherein said movable subperiosteal element is configured so as to allow passage of materials from said periosteal tissue.

88. The device of claim 66, wherein said device is configured to allow passage of materials between the exterior space of said device and the interior space of said device.

89. The device of claim wherein said device is formed at least in part from a stretchable material.

90. The device of claim 66, wherein said device is configured so as to be glued to the tissue.

91. The device of claim 66, wherein said force inducing mechanism is configured so as to induce force by turning a screw.

92. The device of claim 91, wherein said screw is hollow and perforated.

93. The device of claim 66, wherein said device includes an inhibiting component configured to prevent activation of said force inducing mechanism.

94. The device of claim 93, wherein said inhibiting component configured so as to be taken out.

95. The device of claim 94, wherein said inhibiting component is a wire.

96. The device of claim 93, wherein said inhibiting component is formed at least in part from a bio-dissipative material.

97. The device of claim 66, wherein said movable subperiosteal element is formed at least in part from a magnetic material.

98. The device of claim 97, wherein said movable subperiosteal element is enclosed in a biocompatible casing.

99. The device of claim 66, wherein said force inducing mechanism comprising magnetic forces.

100. The device of claim 66, wherein said force inducing mechanism comprising a compressed element trying to become not compressed.

101. The device of claim 100, wherein said compressed element includes a coil.

102. The device of claim 66, wherein said force inducing mechanism includes a material that changes its shape by temperature changes.

103. The device of claim 66, wherein said device includes a reference element and said force inducing mechanism configured so as to induces forces between said reference element and said movable subperiosteal element.

104. The device of claim 103, wherein said reference element is configured so as to be fixated to the bone.

105. The device of claim 104, wherein said reference element is a bone implant.

106. The device of claim 103, wherein said reference element is connected to said movable subperiosteal element by a hinge.

107. The device of claim 106, wherein said hinge configured as to allow movement only in one direction.

108. The device of claim 103, wherein said reference element is configured so as to be fixed to a tooth.

109. The device of claim 103, wherein said reference element is configured so as to be fixed to a dental prosthesis.

110. The device of claim 109, wherein said reference element is formed at least in part from a magnetic material.

111. The device of claim 110, wherein said reference element is configured so as to be gradually displaced.

112. The device of claim 103, wherein said reference element includes a ball socket and said force inducing mechanism includes a screw with a ball at its edge; said ball is configured to fit inside said ball socket forming a joint so as to allow control on the position of said screw.

113. The device of claim 66, wherein said device is a double sheet concave balloon.

114. The device of claim 66, wherein said device is configured so as to prevent movement of said movable subperiosteal element towards said bone.

115. The device of claim 66, wherein at least part of said displacing device is configured so as to be pulled out easily from said tissue.

116. The device of claim 66, wherein said device includes a protruding element configured so as to be connected to said device after insertion subperiostealy and protrude outside the tissue.

117. The device of claim 116, wherein said protruding element is configured to allow connection to other elements.

118. The device of claim 117, wherein said protruding element is configured to allow introducing of materials beneath said movable subperiosteal element.

119. The device of claim 66, wherein said movable subperiosteal element includes fixation element configured so as to attach said movable subperiosteal element to said periosteal tissue.

120. The device of claim 119, wherein said fixation element is in the shape of an arrow.

121. The device of claim 66, wherein said device includes an active biocompatible material enclosed in a bio-dissipative casing.

* * * * *

UNITED STATES PATENT AND TRADEMARK OFFICE
CERTIFICATE OF CORRECTION

PATENT NO. : 6,758,673 B2
DATED : July 6, 2004
INVENTOR(S) : Fromovich et al.

It is certified that error appears in the above-identified patent and that said Letters Patent is hereby corrected as shown below:

Title page,
Item [76], Inventors, "OFIR" appears instead of -- OPHIR --
Item [*] Notice, "bydays.day." appears instead of -- 20 days --

Column 17,
Line 16, -- to allow -- has been omitted between "configured……...ingrowth".

Signed and Sealed this

Fifth Day of July, 2005

JON W. DUDAS
*Director of the United States Patent and Trademark Office*